(12) United States Patent
Hyvarinen

(10) Patent No.: US 8,433,032 B2
(45) Date of Patent: Apr. 30, 2013

(54) ARRANGEMENT AND METHOD IN DIGITAL MAMMOGRAPHY IMAGING

(75) Inventor: Pentti Hyvarinen, Helsinki (FI)

(73) Assignee: Planmed Oy, Helskinki (FI)

( * ) Notice: Subject to any disclaimer, the term of this patent is extended or adjusted under 35 U.S.C. 154(b) by 282 days.

(21) Appl. No.: 12/743,114

(22) PCT Filed: Nov. 14, 2008

(86) PCT No.: PCT/FI2008/050662
§ 371 (c)(1),
(2), (4) Date: Sep. 3, 2010

(87) PCT Pub. No.: WO2009/068732
PCT Pub. Date: Jun. 4, 2009

(65) Prior Publication Data
US 2010/0316186 A1    Dec. 16, 2010

(30) Foreign Application Priority Data
Nov. 14, 2007  (FI) .................................. 20070863

(51) Int. Cl.
*A61B 6/04* (2006.01)
(52) U.S. Cl.
USPC ........................................... 378/37; 378/208
(58) Field of Classification Search .............. 378/37, 378/208, 209
See application file for complete search history.

(56) References Cited

U.S. PATENT DOCUMENTS

| | | | |
|---|---|---|---|
| 5,506,877 A | 4/1996 | Niklason et al. | |
| 5,594,769 A * | 1/1997 | Pellegrino et al. | 378/37 |
| 2004/0125912 A1 | 7/2004 | Wikander | |
| 2005/0063509 A1 | 3/2005 | Defreitas et al. | |
| 2005/0195938 A1 | 9/2005 | Zetterlund | |
| 2007/0030949 A1 | 2/2007 | Jing et al. | |
| 2007/0081625 A1 * | 4/2007 | Sendai | 378/37 |
| 2007/0121782 A1 | 5/2007 | Sendai | |
| 2007/0206723 A1 | 9/2007 | Okada et al. | |

FOREIGN PATENT DOCUMENTS

| | | |
|---|---|---|
| EP | 1772101 A1 | 4/2007 |
| WO | WO 03037046 A2 | 5/2003 |
| WO | WO 2007/034033 A1 | 3/2007 |

OTHER PUBLICATIONS

Goodsitt, M. M., et al., "An Observer Study Comparing Spot Imaging Regions Selected by Radiologists and a Computer for an Automated Stereo Spot Mammography Technique," *Medical Physics*, vol. 31, Issue 6, p. 1558-1567 (May 27, 2004).

International Search Report, PCT/FI2008/050662, date of mailing Apr. 2, 2009.

Finland Search Report, PCT/FI2008/050662, date of mailing May 27, 2008.

* cited by examiner

*Primary Examiner* — Hoon Song
(74) *Attorney, Agent, or Firm* — Hamilton, Brook, Smith & Reynolds, P.C.

(57) ABSTRACT

The invention relates to an arrangement and method in digital mammography imaging especially for use for imaging of small breasts. In the invention, a so-called full-field sensor and an upper compression plate substantially equal in width with this sensor are used. According to the invention, the beam is limited to a width narrower than the width of the sensor and the compression plate and directed for oblique imaging non-centrally relative to the center of said sensor and the upper compression plate, while the automatic exposure system of the imaging apparatus is caused to adapt itself for imaging in accordance with this imaging position non-central relative to the sensor and the upper compression plate.

16 Claims, 5 Drawing Sheets

ARRANGEMENT AND METHOD IN DIGITAL MAMMOGRAPHY IMAGING

Figure 1:
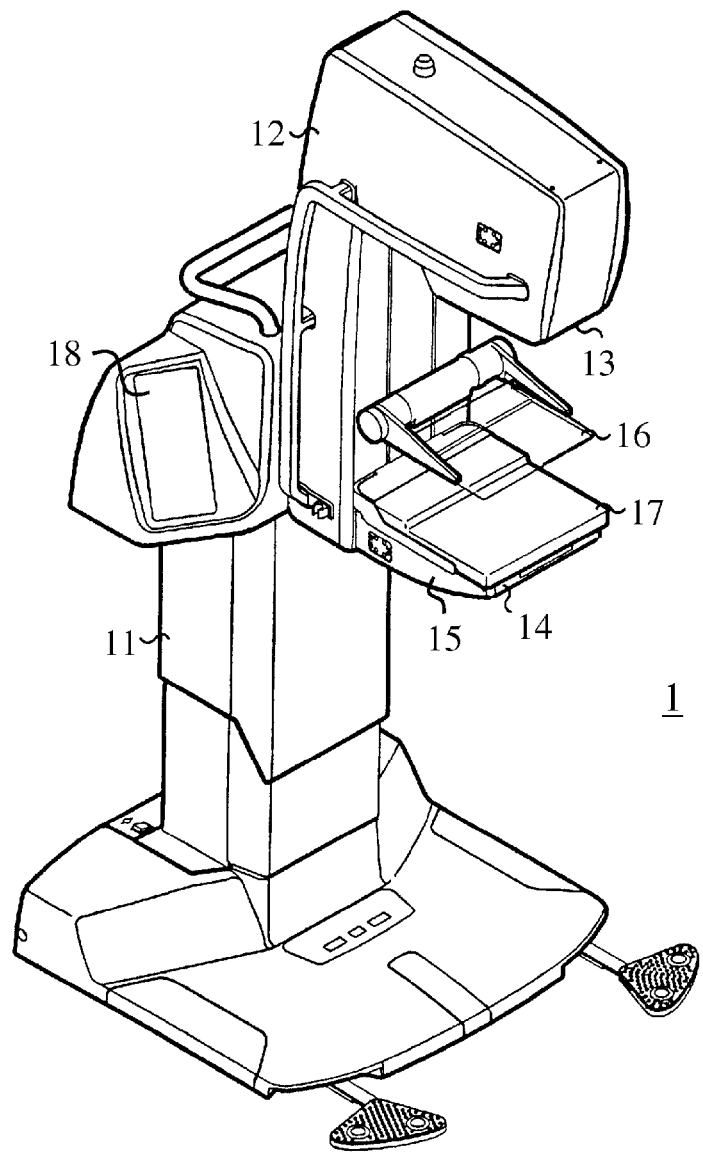

This application is the U.S. National Stage of International Application No. PCT/FI2008/050662, filed Nov. 14, 2008, which designates the U.S., published in English, and claims priority under 35 U.S.C. §§119 or 365(e) to Finland Application No. 20070863, filed Nov. 14, 2007.

The present invention relates to a mammography apparatus arrangement.

Breast cancer is the most common type of cancer in women. According to researches, about one woman in every ten contracts breast cancer at some point in life. In most cases, breast cancer is detected on the basis of symptoms after the patient has sought treatment, but at this time the cancer has often already advanced to a stage where results of the treatment are unsure. Part of the cases of breast cancer are detected in screening studies, which are arranged in several countries for women of e.g. over the age of 40. In screening, often a cancer at a very early stage of development is detected, and consequently its treatment can be started in time and often leads to a positive final result.

Mammography imaging is a widely used method in breast cancer screening as a clinical examination method and also in follow-up monitoring. Mammography imaging is an X-ray breast examination method whereby X-ray imaging is performed using an apparatus specially designed for this purpose. In screening studies, mammography has been reported to have a sensitivity of 90-93% and a specificity of 90-97%. This shows quite clearly that screening studies are very useful and that early detection of breast cancer achieved through them can save human lives. It has been established that mammography reduces breast cancer mortality by 35 percent among women of over 50 years and by 25-35 percent among women between 40-50 years of age.

In typical mammography imaging, the breast is compresses in a mammography apparatus between two compression plates, or e.g. between an as immovable arranged imaging table and a movable compression plate arranged above it. Typically, at least two radiographs are taken of the breast thus compressed, one from above and another from an oblique direction (oblique projection). If necessary, an additional third image is taken directly from the side. In mammography, various anomalies such as calcifications, which are small calcium deposits in soft breast tissue, are searched for. A calcification can generally not be detected by palpation, but it is visible in mammography. Large calcifications are generally not related to cancer, but clusters of tiny calcifications, i.e. so-called micro-calcifications are an indication of excessive breast cell activity, which may be related to breast cancer. Other structures to be looked for include cysts and fibroadenomas which, however, are generally not related to cancer.

In mammography, too, the use of film is increasingly being replaced by digital imaging technology. Due to differences in breast size, it has been customary in the film era to use film cassettes of typically two different standard sizes. However, as especially large digital sensors are very expensive and repeated replacement of sensors by differently-sized sensors is not necessarily as easy to arrange as replacement of film cassettes, there has been a trend towards using in the mammography apparatus only a one size of a sensor. To enable imaging of large breasts as well with the same apparatus, it is necessary to employ either scanning imaging techniques or a large, so called full-field sensor, the size of which corresponds to the 300×240 mm size known in the film technology.

However, in addition to its high cost, the use of a large sensor also brings along various other problems. One of the problems is the situation where so-called oblique images of small breasts should be taken. In oblique imaging, the edges of the sensor, and those of a compression plate of a size corresponding to the sensor size, settle themselves in the armpit of the person being imaged. In this situation, correct positioning of a small breast between the compression plates is problematic as it is difficult to reach it practically from any direction. Moreover, if a beam corresponding to the sensor size is used, the digital image taken of a small breast will be rich in areas having received direct radiation as well, which according to regulations of this field still cannot be removed from the image even later. Thus, the image files will be quite large as in addition to actual image information, they will also contain a large amount of information that is completely useless in view of the objective of the imaging. On the other hand, limiting the beam so as to make it narrower than a full-field sensor is not a really workable alternative, either, because when—as stated above—in the oblique imaging position the edges of the sensor and the compression plate are positioned in the armpit of the person being imaged, the situation is likely to become such that, due to anatomic reasons, it is not possible to position the breast, at least not the whole breast, in the area covered by a beam limited to be narrower than the sensor.

To alleviate the problems encountered in oblique imaging with a full-field sensor, solutions have been developed in which, especially in the case of a small breast, a compression plate designed expressly for smaller breast sizes, i.e. a compression plate that is substantially narrower than a full-field sensor, and on the other hand a beam limited to a corresponding size, are used in the imaging apparatus. By arranging for a compression plate like this to be laterally movable and the size and, correspondingly, position of the beam to be adjustable, the compression plate can be positioned in oblique imaging mode non-centrally on the full-field sensor, i.e. e.g. at the corner of the sensor, and the X-ray beam collimated correspondingly. An arrangement of this type, the introduction of which requires significant changes in the structures of the mammography apparatus and, on the other hand, in practice necessitates e.g. repeated changing and removal of compression plates, is proposed i.a. in WO publication 03/037046.

The current invention is directed to improving the state of the art and providing; a new type of mammography X-ray apparatus arrangement and method to enable easier positioning of especially small breasts for oblique imaging, when a large so called full-field sensor is used.

The invention is characterized by what is disclosed in the attached claims.

The solution of the invention has the advantage that setting up the imaging arrangement in a manner suited for oblique imaging of small breasts does not require the extra operations involved when the compression plate is moved and/or compression plates are changed, while still allowing images to be produced that do not contain such a large amount of completely useless information occupying recording capacity and slowing down transfer of images, as is the case when small breasts are imaged with a full-field sensor using a beam substantially corresponding to the size of the sensor. On the other hand, thanks to the invention, e.g. the complexity of the mammography apparatus need not be increased, at least not as far as would be necessary if the compression plate were arranged to be laterally movable.

Figure 2:
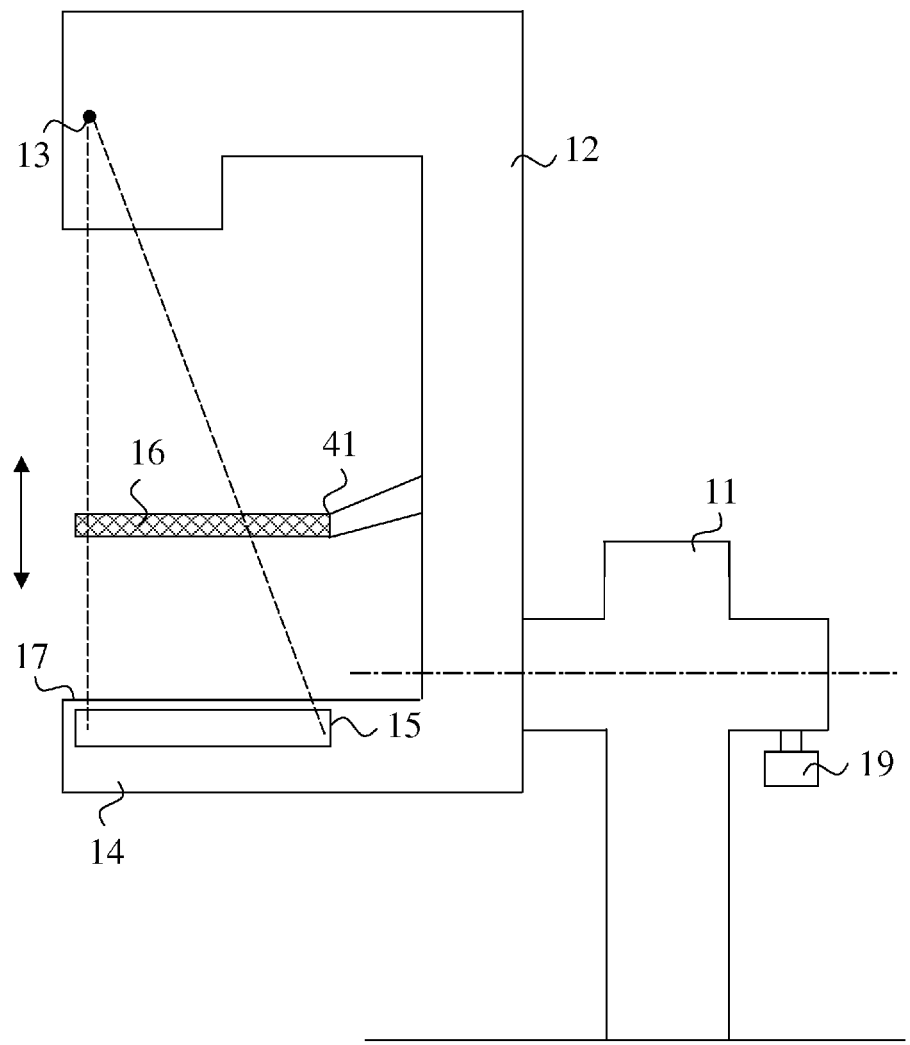
Figure 3:
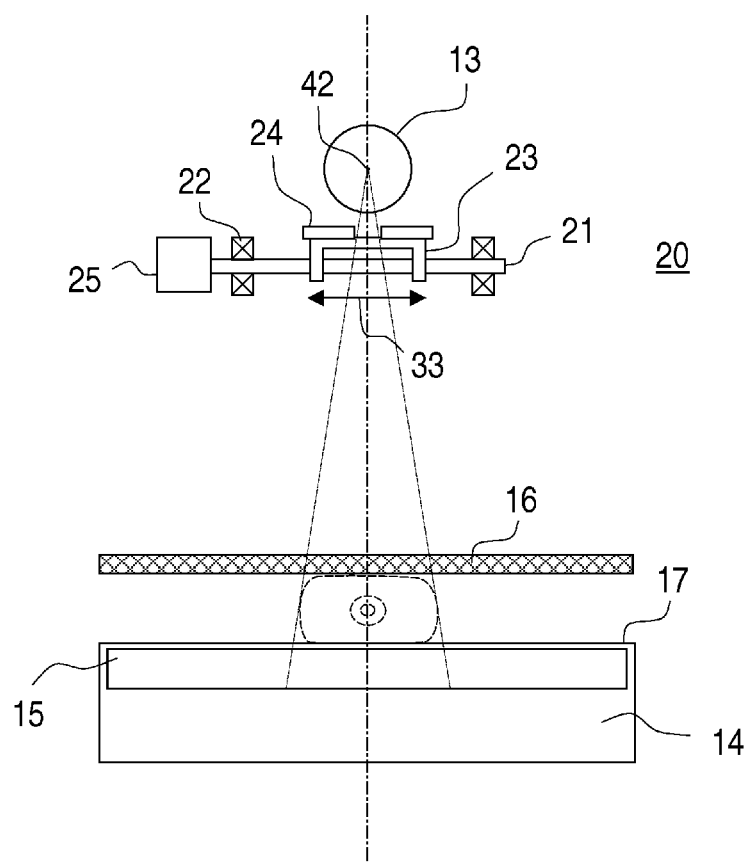
Figure 4:
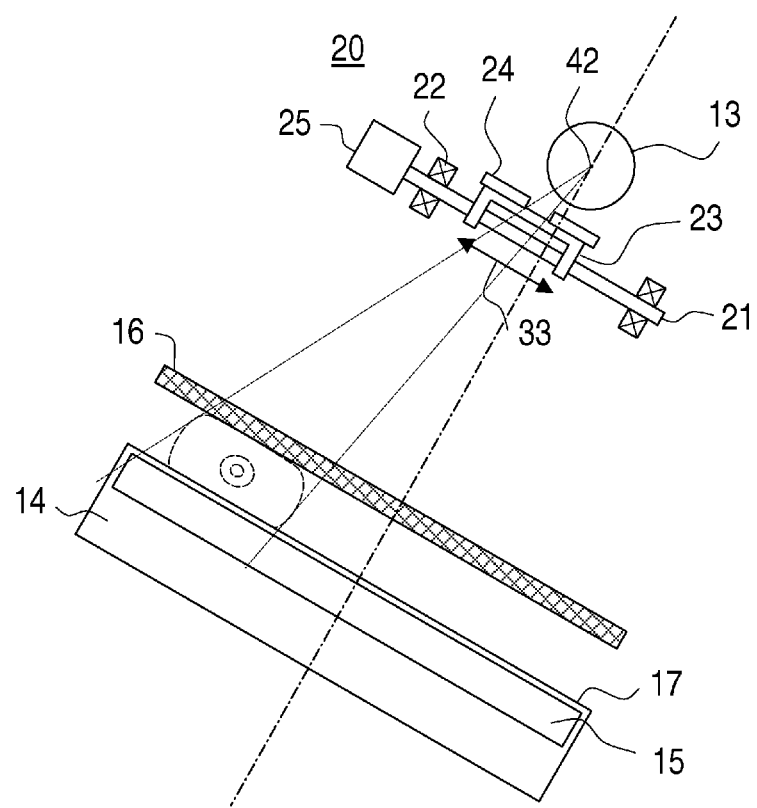
Figure 5:
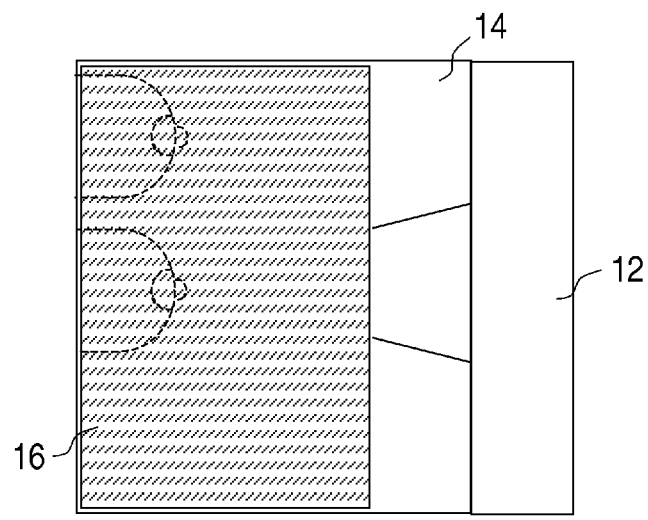
Figure 6:
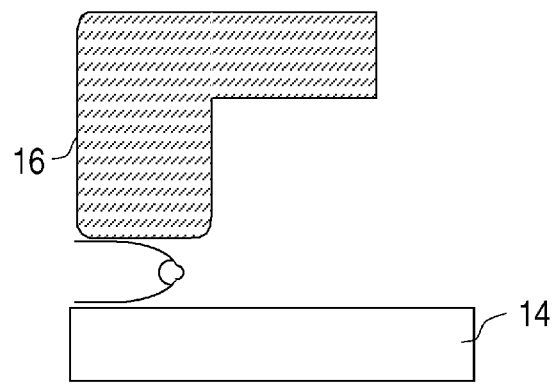

In the following, the invention will be described in greater detail and by also referring to the attached figures, wherein FIG. 1 presents a general view of a typical mammography X-ray apparatus, FIG. 2 presents certain typical structures of a mammography X-ray apparatus in side view, FIG. 3 presents a mammography imaging arrangement in the case of imaging performed in a normal vertical orientation, FIG. 4 presents an oblique imaging arrangement according to the invention, FIG. 5 presents ways in which the tissue to be imaged is positioned according to FIGS. 3 and 4 in a view seen directly from above, and FIG. 6 presents a specific compression plate applicable for use in the invention.

The mammography X-ray apparatus 1 presented in FIG. 1 consists of a frame part 11 and an arm part 12 connected to it, often called a C-arm. Typically, placed at opposite ends of the C-arm are a radiation source 13 and image data receiving means 15 mounted e.g. inside a so-called lower shelf structure 14, which imaging means 13, 15 as being disposed inside the cover of the apparatus are not actually visible in FIG. 1. In addition, means 16, 17 for positioning the object to be imaged in the imaging area is disposed in the area between the imaging means 13, 15, typically near the image data receiving means 15. The C-arm 12 is typically both movable in a vertical direction to vary the height position of the means 16, 17 for positioning the object to be imaged, and rotatable relative to the frame part 11. The positioning means 16, 17 typically consist of an upper compression plate 16 and a lower compression plate 17, and this lower compression plate 17 may also be arranged to function as a so-called bucky. "Bucky" refers to a grid structure placed between the tissue to be imaged and the image data receiving means 15 to restrict the radiation scattered from the tissue from reaching the image data receiving means. Often the apparatus has no separate lower compression plate component 17, but instead the surface 17 of the lower shelf 14 functions itself as a lower compression plate. In addition, the apparatus comprises a control system, to which it is possible to transmit control signals e.g. from a control panel 18.

FIG. 2 presents one typical mammography apparatus in side view. FIG. 2 shows the frame part 11 of the apparatus, the C-arm 12, the radiation source 13 and the lower shelf structure 14, over which the breast to be imaged will be compressed and held immovable by means of an upper compression plate 16 arranged to be movable in the vertical direction of the C-arm 12. The figure also shows an imaging sensor 15 disposed inside the lower shelf structure 14 and an actuator (motor) 19 for rotating the C-arm. In addition, the apparatus typically comprises a collimator, which is arranged in the immediate vicinity of the radiation source 13 to limit the beam, but, for the sake of clarity of the drawing, the collimator is not shown in FIG. 2. One embodiment of the collimator 20 is presented by way of example in connection with FIGS. 3 and 4.

FIG. 3 illustrates collimation of the beam to substantially the same size with the object to be imaged, and for directing it to the object when imaging is implemented in a normal vertical C-arm orientation. In FIG. 3, the object to be imaged is compressed and held immovable by means of an upper compression plate 16 having a width substantially equal to the width of the sensor 15, and the radiation obtained from the focus 42 of the radiation source 13 is limited substantially to the size of the object by a collimator structure 20.

The collimator structure 20 according to FIG. 3 comprises a collimator plate pair 24 arranged to be moved by an actuator 25, such as a motor, which rotates a bearing-mounted screw 21. Arranged in connection with the collimator plates 24 are protrusions 23 or equivalent, which are provided with an internal thread adapted to the screw 21, so that when the screw 21 is rotating, the collimator plate structure 24 moves in the direction of the center axis of the screw 21. In FIG. 3, the directions of motion of the collimator 20 are indicated by an arrow 33.

FIG. 3 presents one arrangement that allows variation of the position of the beam, but as many other arrangements allowing changing position of the beam, as well as many other solutions permitting changing size and/or shape of the beam are clear to a person skilled in the art, they will not be described in further detail in this connection.

FIG. 4 illustrates how the tissue to be imaged is positioned and the beam collimated non-centrally in the oblique imaging arrangement of the invention. By observing FIG. 4, one can also easily perceive how the left edge of the lower shelf 14 and that of the compression plate 16 are positioned in the area of the arm-pit of the person being imaged not shown in the figure, and further how in this situation, especially in the case of smaller breasts, it easily happens that if the beam were collimated to the middle of the full-field sensor 15 as illustrated in FIG. 3, at least part of the tissue intended to be imaged would easily be left outside the area getting imaged.

FIG. 5 shows the positions of the object to be imaged according to FIGS. 3 and 4 as seen perpendicularly from above the upper compression plate 16, i.e. a top-view illustration of the way in which the tissue to be imaged is positioned in these cases on the lower shelf structure 14. We can thus see from these figures how the collimator arrangement 20 directs the beam when images are taken in the vertical orientation of the C-arm 12 so that the center axis of the beam positions substantially on the center of the sensor 15 and upper compression plate 16, whereas in oblique imaging the center axis of the beam does not position on the center of the sensor 15 or the compression plate 16 but is directed non-centrally, preferably so that the beam is directed essentially to a corner of the sensor 15.

As it is one object of the arrangement of the invention to enable use of a mammography apparatus having a full-field sensor for the imaging of both small and large breasts, and then especially in oblique orientation as well, the collimation means 20 used in the apparatus may be arranged to comprise e.g. an adjustable collimator arrangement to allow the width of the beam to be adjusted to at least two predetermined standard widths. The collimation means 20 may comprise e.g. a replaceable collimator plate arrangement 24 and/or a collimator plate arrangement 24 having at least two openings and/or slots of different sizes and/or shapes.

The imaging arrangement of the invention is preferably provided with means for recognizing the orientation of the C-arm 12 conforming with a predetermined oblique imaging position and a means for sending a signal indicating this recognition to the control system of the apparatus. The arrangement is also preferably provided with a means, such as a function key in a control panel 18, for transmitting to the control system information indicating that a small breast is going to be imaged. In response to such information, the control system may then be arranged to automatically control the collimator arrangement 20 of the apparatus in such a way that the beam is limited to a size smaller than the surface area of the full-field sensor 15, and correspondingly smaller than the surface area of the compression plate 16 having a width substantially equal to that of the full-field sensor 15, and that the beam is directed e.g. to a predetermined place near the edge of the sensor 15—especially to that corner of the front edge of the sensor 15 which is turned up in the oblique imaging orientation of the C-arm 12.

The control system may also comprise means for collimating the beam for the imaging of a small breast in other ways than in a predetermined manner, according to control commands issued either from the control panel 18 or from some other user interface. The control system may comprise means, such as dedicated keys and/or certain key sequences and/or key combinations arranged in the control panel 18, by means of which the operator can choose to which corner of the sensor 15 the beam is to collimated, or whether it is to be collimated to the center. The arrangement may also comprise means for directing the beam to areas other than expressly the aforementioned three predetermined points and, on the other hand, for adjusting the size and/or shape of the beam in other directions besides the width-wise direction. The adjustment of the beam may be arranged to comprise several specific types of beams, and it may also be arranged to function steplessly.

In particular, the collimation means of the invention are arranged to allow a beam limited to a size smaller than the surface area of a full-field imaging sensor 15, and that of an upper compression plate 16 having the same width with it, to be limited to a width narrower than that of the full-field imaging sensor 15 and to enable the beam to be directed, on the one hand, to the center of the sensor and, on the other hand, to at least either of those of its corners whose other side is set against the patient's chest when the patient is being positioned for imaging.

In one preferred embodiment of the invention, the mammography apparatus comprises a control system and a control panel 18 functionally connected to it, by means of which control system and control panel, especially when small breasts are to be imaged, it is possible to supply to the apparatus a control signal for executing a combination of actions, which comprises operating the actuator 19 rotating the C-arm part 12 so as to cause the arm part 12 to assume a predetermined oblique-imaging position, and controlling the collimator structure 20 in such a way that it limits the beam to an area of a size smaller than the surface area of the full-field imaging sensor 15, and of the compression plate 16 of substantially the same width used in the apparatus according to the invention, and directs the beam to such a predetermined place on the sensor 15 and correspondingly on the compression plate 16 at which the center axis of the beam does not coincide with the center axis of the sensor and the compression plate. Essentially, also the automatic exposure system used in the mammography apparatus is arranged to adapt itself to receive and/or read a signal from that area smaller than the surface area of the full-field imaging sensor to which the beam has been directed for performing the imaging. This combination of actions may preferably be arranged to be carried out in response to one or more control signals issued e.g. from the control panel 18 of the apparatus. The control signal in question may also be based on identifying e.g. the circumstance that the C-arm part 12 has been moved or is being moved to a predetermined oblique imaging orientation.

In one embodiment of the invention, the mammography apparatus comprises a connector structure 41 for the compression plate 16, which connector structure 41—not presented in detail in the attached drawings—has been arranged to enable at least two different compression plates 16 to be connected to the arrangement and means arranged in functional connection with the connector structure 41 for detecting the connection of at least one compression plate 16 of predetermined type to said connector structure 41. The above-described combination of actions can thus be arranged to be carried out in response to detection of a compression plate 41 of predetermined type, either directly or in association with detection of the C-arm 12 being or having been moved to a predetermined oblique imaging orientation.

FIG. 6 presents one possible compression means 16 arranged to be identified according to the invention, comprising at least two portions of different thicknesses, of which the thickest portion is disposed in the area of that end of the compression means 16, which positions towards the chest of the person being imaged. A compression means 16 like this can advantageously be used expressly when small breast are imaged using a full-field sensor 15. The thinner portion of this compression means 16 makes positioning of the tissue between the compression plates 16, 17 (compression surfaces) easier, as the tissue can be manipulated at least through the thinner area of the compression means 16.

The arrangement of the invention is preferably implemented using an automatic exposure system which, instead of a separate automatic exposure sensor or sensors, is based on information read from the imaging sensor itself. According to the invention, adaptation of the automatic exposure function in a manner consistent with the area arranged to be imaged is based on selecting expressly that portion of the sensor area for the automatic exposure function to which the beam is directed according to the invention.

The arrangement of the invention may also comprise a function wherein the size of the focus 42 of the radiation source 13 used for imaging is selected automatically by the control system of the apparatus on the basis of the control system recognizing that the apparatus is positioned to take an image of a given type.

Accordingly, in an exemplary method of the invention, a mammography apparatus having a radiation source and a C-arm comprising a so-called full-field sensor is used for mammography imaging, in which method the object to be imaged is positioned for imaging in the area between the aforesaid full-field sensor and a compression plate of substantially the same width with it, the radiation generated by the radiation source is limited to form a beam smaller than the surface area of the full-field sensor and the compression plate of substantially the same width with it and directed towards the sensor, in which method at least one imaging parameter is controlled by an automatic exposure function, and in which method the C-arm is moved into an oblique imaging position, which may he a predetermined angular position, the beam is limited to cover an area smaller than the surface area of the aforesaid full-field imaging sensor, and correspondingly of the aforesaid compression plate, and directed to such a predetermined area of said sensor and said compression plate at which the center axis of the beam does not position at their center. Further, the automatic exposure system of the apparatus is adapted to receive and/or read a signal from the aforesaid area smaller than the surface area of the full-field imaging sensor to which the beam has been directed. At least some of these actions can be carried out by issuing from a control panel, or a corresponding user interface provided in the mammography apparatus, one or more control signals to the control system of the mammography apparatus.

Further, the control system of the mammography apparatus can be arranged to identify a situation where the arm part 12 is being moved to a predetermined angular position and, in response to recognition thereof, to limit the beam to cover an area smaller than the surface area of the full-field imaging sensor 15, and of the compression plate 16 having substantially the same width with it, and to direct it to such a predetermined area of the sensor 15 and correspondingly of the compression plate 16 in which the center axis of the beam does not position at the center of the sensor 15, nor at the center of the compression plate 16. The beam is preferably so directed that it positions substantially at such a sensor corner whose other side is set against the chest of the patient when the patient is being positioned for imaging. The automatic exposure system of the mammography apparatus is also arranged to receive and/or read a signal from the aforesaid area smaller than the surface area of the full-field imaging sensor to which the beam has been directed.

Further, in a possible procedure according to the invention, the mammography apparatus is provided with a compression plate 16 comprising, in that front part of the compression plate 16 which is positioned against the chest, a portion that is thicker than at least one portion behind and/or beside said front part, the arm part 12 of the mammography apparatus is moved into an oblique imaging orientation and the tissue to be imaged is positioned in the mammography apparatus by compressing it under the aforesaid thicker portion of the compression plate 16 so that at least more than half of the tissue to be imaged is positioned in the area of that half the full-field sensor 15, which in the aforesaid oblique imaging position has been turned to a position higher than the center of the sensor. The exposure of the tissue to be imaged is then implemented by limiting the beam by means of a collimator arrangement 20 provided in the mammography apparatus so that the beam positions on the area where the tissue to be imaged has been positioned. The exposure is implemented by utilizing an exposure automation signal which has been arranged to be obtained or read from that full-field sensor area apart from the center of the sensor 15 wherein the tissue to be imaged has been positioned.

It is obvious to a person skilled in the art that the invention is not exclusively limited to the examples described above but that it may be varied within the scope of the claims presented below, and thus e.g. the structure of the mammography apparatus may differ from that described above in a general form.

The invention claimed is:

1. A mammography apparatus arrangement for imaging both small and large breasts, comprising an arm part rotatable by an actuator, a radiation source arranged in connection with the arm part, a collimation means for limiting the radiation produced by the radiation source to form a beam and directing the beam to the object to be imaged, a so-called full-field imaging sensor and a laterally unmovable upper compression plate fixed to the arm part so as to follow rotation thereof, the upper compression plate having a width substantially equal to the width of said full-field imaging sensor arranged in the area between the radiation source and the full-field imaging sensor, an automatic exposure system, a control system and a control panel or other user interface functionally connected to it, wherein the arrangement comprises means for implementing in response to one or more control signals, a combination of automatic operation actions which are useful for imaging small breasts and comprises, i) operating the actuator rotating the arm part so as to cause the arm part to assume a predetermined oblique imaging position, ii) positioning of the aforesaid collimation means in such a way that they limit the beam to a predetermined area of the full-field imaging sensor that is smaller than the surface area of the full-field imaging sensor and that of the upper compression plate substantially equal in width with it, and iii) directing the beam to the predetermined area of the full-field imaging sensor so that the center axis of the beam does not position at the center of said sensor, and correspondingly of the compression plate, and iv) adapting said automatic exposure system to receive and/or read a signal from the aforesaid area smaller than the surface area of the full-field imaging sensor whereto the beam is directed.

2. The mammography apparatus arrangement according to claim 1, wherein it is arranged to carry out the aforesaid combination of actions in response to a control signal issued from said control panel or a corresponding user interface.

3. The mammography apparatus arrangement according to claim 1, wherein the number of aforesaid control signals is one and said signal is based on identifying the circumstance that said arm part has been moved or is being moved to a predetermined oblique imaging orientation.

4. The mammography apparatus arrangement according to claim 1, wherein the arrangement comprises a connector structure for the upper compression plate, said connector structure being arranged to enable at least two different upper compression plates to be connected to the arrangement, and means arranged in functional connection with the connector structure for detecting the connection of at least one compression plate of predetermined type to said connector structure, and that the arrangement has been arranged to carry out the aforesaid combination of actions in response to a control signal which at least partly consists of detecting the connection of an upper compression plate of predetermined type to the arrangement.

5. The mammography apparatus arrangement according to claim 4, wherein the aforesaid upper compression plate arranged to be detected comprises at least two portions differing from each other in thickness, of which the thickest portion is disposed substantially in the area of that end of the compression means which, when connected to the arrangement, is positioned towards the chest of the person being imaged.

6. The mammography apparatus arrangement according to claim 1, wherein the aforesaid automatic exposure system is based on information read from said full-field imaging sensor and the aforesaid adaptation of the automatic exposure function comprises selecting for automatic exposure that sensor area to which the beam is directed.

7. The mammography apparatus arrangement according to claim 1, wherein the aforesaid collimator means comprise an adjustable collimator arrangement for adjusting the width of the beam to at least two predetermined standard widths.

8. The mammography apparatus arrangement according to claim 1, wherein the aforesaid collimation means comprise a replaceable collimator plate arrangement and/or a collimator arrangement having at least two openings and/or slots of different size and/or shape.

9. The mammography apparatus arrangement according to claim 1, wherein said collimation means is arranged to enable the beam to be limited to a size smaller than. the surface area of said full-field imaging sensor, and of the upper compression plate substantially equal in width with it, so that the beam is limited to a width narrower than the width of the full-field imaging sensor, and to enable the beam to be directed, on the one hand, to the center of said sensor and, on the other hand, to at least the other of those corners of the sensor whose other side positions against the chest when the patient is being positioned for imaging.

10. A method in connection with digital mammography imaging, in which the imaging is performed using a mammography apparatus suitable for imaging both small and large breasts having a radiation source and a rotatable arm part comprising a so-called full-field imaging sensor fixed thereto, in which method the object to be imaged which comprises at least one of small and large breasts, is positioned for the imaging in the area between the aforesaid full-field imaging sensor and a laterally unmovable compression plate of substantially equal width with the full-field imaging sensor and fixed to the aim part so as to follow rotation thereof, the radiation produced by the radiation source is limited to form a beam and directed towards the imaging sensor, and in which method at least one imaging parameter is controlled by an automatic exposure system, wherein the method comprises in response to one or more control signals automatically i) moving the C-arm into a predetermined oblique imaging position, ii) limiting the beam to cover a predetermined area of the full-field imaging sensor that is smaller than the surface area of the full-field imaging sensor and that of the compression plate of substantially equal width with it, iii) directing the beam to such predetermined area of said full-field imaging sensor and of said compression plate of substantially equal width with it in which the center axis of the beam does not position on their center and iv) adapting the aforesaid automatic exposure system to receive and/or read a signal from the aforesaid area smaller than the surface area of the full-field imaging sensor to which the beam is directed.

11. The method according to claim 10, wherein at least one of said one or more control signals is issued from a control panel or from a corresponding user interface arranged in the mammography apparatus.

12. The method according to claim 11, wherein the control system of the mammography apparatus is arranged to recognize a situation where the arm part is being moved to a predetermined angular position and, in response to this recognition, the beam is limited to cover an area smaller than the surface area of the full-field imaging sensor and of the compression plate substantially equal in width with it, and the beam is directed to a sensor area where the center axis of the beam does not position on the center of the sensor nor on the center of the compression plate arranged to be substantially equal in width with it.

13. The method according to claim 10, further comprising providing the mammography apparatus with a compression plate that comprises in its front part positioned against the chest a portion that is thicker than at least part of the portion or portions behind and/or beside said front part; moving the arm part of the mammography apparatus into an oblique imaging position; positioning the tissue to be imaged in the mammography apparatus by compressing it under the aforesaid thicker portion of the compression plate so that at least more than half of the tissue to be imaged is positioned in the area of that half the full- field sensor which in the aforesaid oblique imaging position has been turned to a position higher than the center of the sensor.

14. The method according to claim 10, wherein the beam is limited to a width narrower than the aforesaid imaging sensor, 15. The method according to claim 10, wherein the beam is directed to such a corner of said imaging sensor whose other side positions itself against the chest when the patient is being positioned for imaging.

16. The method according to claim 10, wherein the beam is directed to that side of the center of said imaging sensor which in the oblique imaging orientation of the aforesaid arm part is turned to lie higher.

* * * * *

UNITED STATES PATENT AND TRADEMARK OFFICE
CERTIFICATE OF CORRECTION

PATENT NO. : 8,433,032 B2
APPLICATION NO. : 12/743114
DATED : April 30, 2013
INVENTOR(S) : Pentti Hyvarinen It is certified that error appears in the above-identified patent and that said Letters Patent is hereby corrected as shown below:

On the Title Page

In Assignee Item (73), delete "Helskinki" and insert --Helsinki--.

In the Specifications

In Column 1, bridging Lines 38-39, delete "compresses" and insert --compressed--.

In Column 5, Line 11, between "to" and "collimated", insert --be--.

In the Claims

In Column 8, Claim 9, Line 48, between "than" and "the", delete ".".

In Column 8, Claim 10, Line 67, delete "aim" and insert --arm--.

Signed and Sealed this
Sixth Day of August, 2013

Teresa Stanek Rea
*Acting Director of the United States Patent and Trademark Office*